United States Patent [19]

Casse et al.

[11] Patent Number: 5,756,803
[45] Date of Patent: May 26, 1998

[54] PROCESS FOR THE CONDENSATION OF AN ALDEHYDE WITH HYDROGEN CYANIDE

[75] Inventors: Claude Casse, Decines Charpieu; Frédéric Kress, Vienne; Philippe Morel, Chuzelles, all of France

[73] Assignee: Rhone-Poulenc Nutrition Animale, Antony, France

[21] Appl. No.: 637,120

[22] Filed: Apr. 24, 1996

[30] Foreign Application Priority Data

Apr. 24, 1995 [FR] France ................... 95 04865

[51] Int. Cl.$^6$ .................. C07C 253/30; C07C 321/04
[52] U.S. Cl. .................. 558/351; 558/315; 558/341; 562/559; 562/869; 568/458; 568/492
[58] Field of Search .................. 562/559, 869; 568/458, 492; 558/351, 315, 341

[56] References Cited

U.S. PATENT DOCUMENTS

| | | |
|---|---|---|
| 2,745,745 | 5/1956 | Blake et al. |
| 3,931,307 | 1/1976 | Eikelmann et al. ........... 260/534 S |
| 4,518,801 | 5/1985 | Bolze et al. |
| 4,912,257 | 3/1990 | Hernandez et al. |
| 4,960,932 | 10/1990 | Gillonnier et al. |

FOREIGN PATENT DOCUMENTS

WO94/08957  4/1994  WIPO.

OTHER PUBLICATIONS

Ziegler et al., "Ein einfacher Zugang zu (R)–a–Hydroxycarbonsäuren und (R)–1–Amino02–alkoholen aus (R)–Cyanhodrinen", Synthesis, 7:575–578 (1990).

Ognyanov et al., "Preparation of Chiral Cyanohydrins by an Oxynitrilase–Mediated Transycanation", Journal of the American Chemical Society, 113(18):6992–6996 (1991).

Pierson et al., "Synthesis of DL–Methionine", The Journal of the American Chemical Society, 70(4):1450–1451 (1948).

Lu et al., "A Simple total Synthesis of Naturally Occuring Hydroxy–amino Acids by Enzymatic Kinetic Resolution", Tetrahedron:Asymmetry, 4(5):893–902 (1993).

Zandbergen et al., "Synthesis of Optically Active Cyanohydrins Using Almond Meal", Synthetic Communications, 21(12 & 13);1387–1391 (1991).

Tellitu et al., "A Simple Enzymatic Synthesis of (3S, 4R)–(+)–4–Hydroxy–3–phenyltetrahydroisoquinolines", Tetrahedron:Asymmetry, 5(8):1567–1578 (1994).

Brussee et al., "Synthesis of Optically Active Silyl Protected Cyanohydrins", Tetrahedron, 46(3) :979–986 (1990).

"J. Other Carbon Nucleophiles—The Formation of Cyanohydrins," *Advanced Organic Chemistry*, Jerry March, Fourth Ed., John Wiley & Sons (1993), pp. 964–965.

"Cyanohydrins," *Encyclopedia of Chemical Technology*, Third Edition, vol. 7, Kirk–Othmer; John Wiley & Sons (1979), pp. 386–395.

*Primary Examiner*—Johann Richter
*Assistant Examiner*—Jane C. Oswecki
*Attorney, Agent, or Firm*—Finnegan, Henderson, Farabow, Garrett & Dunner, L.L.P.

[57] ABSTRACT

A process for the condensation of an aldehyde with hydrogen cyanide in the presence of a buffer is disclosed. The buffer advantageously allows the condensation reaction to occur at a pH equal to or above 4.0 and in the absence of amines.

21 Claims, 1 Drawing Sheet

PROCESS FOR THE CONDENSATION OF AN ALDEHYDE WITH HYDROGEN CYANIDE

BACKGROUND OF THE INVENTION

The present invention relates to novel catalysts useful for the condensation of an aldehyde with hydrogen cyanide. The present invention also relates to a process for the condensation of hydrogen cyanide with an aldehyde.

It has been known, for example according to U.S. Pat. No. 4,518,801, to prepare methionine by hydrolysis of 5-(β-methyl-mercaptoethyl)hydantoin in the presence of from 0.3 to 5 equivalents of alkaline hydroxide, of alkaline carbonate or of a mixture thereof, then to separate the alkaline methioninate obtained from the salts coproduced during the hydrolysis and, lastly, to hydrolyse the alkaline salt obtained to produce methionine. The hydantoin compound is prepared by contact between the cyanohydrin of methylthiopropionic aldehyde, ammonia and carbon dioxide.

It has also been known, for example according to U.S. Pat. No. 4,960,932, to prepare methionine by a process comprising four steps. In the first step, methylthio-α-hydroxybutyronitrile is prepared by condensation of methylthiopropionic aldehyde and hydrogen cyanide in the presence of triethylamine. In a second step, the methylthio-α-hydroxybutyronitrile is placed in contact with ammonia in order to form methylthio-α-aminobutyronitrile, which is then hydrolysed in a third step in the presence of a ketone and an alkaline hydroxide in order to form methylthiobutyramide, which is finally hydrolysed to alkaline methioninate and then saponified with an acid in a fourth step.

In the case of the preparation of methylthio-α-hydroxybutyric acid, also referred to as the hydroxy analogue of methionine, the methylthio-α-hydroxybutyronitrile obtained by reaction of methylthiopropionic aldehyde with hydrogen cyanide, in a medium containing pyridine or an amine (see U.S. Pat. No. 2,745,745, column 2, lines 52 to 55), is hydrolysed by sulphuric acid in order to form methylthio-α-hydroxybutyramide as an intermediate and, finally, methylthio-α-hydroxybutyric acid (see European Patent No. 330,527 or U.S. Pat. No. 2,745,745).

The bases used when methylthiopropionic aldehyde is placed in contact with hydrogen cyanide increase the rate of reaction, but rapidly bring about a degradation of the cyanohydrin formed and a degradation of the starting aldehyde, with formation of a highly colored solution. In addition, these bases are volatile and toxic, which is a great handicap during industrial exploitation since their use requires recycling and safety conditions that are always expensive. In addition to these drawbacks, the volatility of these bases may give rise to local accumulations making the medium very basic in places, thereby giving rise to an increase in coloration, on the one hand, by polymerization of the hydrogen cyanide and, on the other hand, by degradation of the methylpropionic aldehyde.

It was seen, quite surprisingly, that the degradation reaction could be reduced and the condensation reaction promoted if the process was performed in a well-defined pH region and in the absence of the amines always used in the prior art.

SUMMARY OF THE INVENTION

The present invention thus relates to the condensation of an aldehyde with hydrogen cyanide in the presence of a buffer that makes it possible to use a pH for the reaction equal to or above 4.0, without using any amines in the reaction. The pH of the reaction preferably ranges from 4.0 to 6.0. The pH of the reaction is even more preferably about 5.

According to a preferred way of carrying out the invention, in order to allow the catalysis of a reaction by reactive absorption, that is to say by contact between a gas, such as hydrogen cyanide, and a liquid, such as methylthiopropionaldehyde, a buffer is preferred which is preferably non-volatile and non-toxic, in contrast with the volatile amines used in the prior art.

The term "buffer" as used in this application is defined as a substance or mixture of substances (as acid salts of weak acids or amphoteric substances) that in solution is capable of neutralizing within limits both acids and bases and thus acts to maintain the original hydrogen-ion concentration of the solution.

Among the buffers which make it possible to set the pH in the region desired, it is preferable to use a buffer chosen from the following mixtures which are mentioned as examples and do not constitute limitations of the invention: citric acid and sodium citrate; citric acid and sodium hydroxide; phosphoric acid and sodium hydrogen phosphate; phosphoric acid and sodium hydroxide; succinic acid and sodium succinate; succinic acid and sodium hydroxide; acetic acid and sodium acetate; acetic acid and sodium hydroxide; and potassium hydrogen phthalate and sodium hydroxide.

Mixtures of acid and alkaline salts of acid or mixtures of acid and alkaline hydroxide may more generally be used as a buffer.

The use of a buffer conveys the advantage, on the one hand, of avoiding the degradation of the starting material and the desired product and, on the other hand, of neutralizing the hydrogen cyanide stabilizing acids, such as sulphuric acid.

Among the aldehydes, it is preferable to use aliphatic aldehydes containing from 1 to 6 carbon atoms that may be unsubstituted or substituted with an alkyl, alkoxy or alkylthio group. It is more preferable to use methylthiopropionic aldehyde.

According to a preferred way of carrying out the invention, the buffer is prepared in situ by neutralization of citric acid with sodium hydroxide according to a citric acid/sodium hydroxide molar ratio ranging from 0.3 to 0.7 and preferably being about 0.5.

According to another preferred way of carrying out the invention, a gaseous mixture of hydrogen cyanide containing about 7% by volume of hydrogen cyanide and an aqueous solution of aldehyde are used according to the first technique for the condensation. The hydrogen cyanide is preferably prepared according to the well-known Andrussow process and is then freed of the ammonia contained therein.

According to a third preferred way of carrying out the invention, an aqueous solution of hydrogen cyanide in water containing about 20% by weight of hydrogen cyanide is placed in contact with an aldehyde. The molar ratio between the hydrogen cyanide and the aldehyde is preferably in slight excess with respect to hydrogen cyanide. It is thus preferred to use a molar excess ranging from 0.1 to 10%, and even more preferably a molar excess ranging from 2 to 5%.

The buffer used as a condensation catalyst is used so as to set the pH in the desired region. The buffer is preferably used, for example, for the citric-citrate buffer, in a molar ratio relative to the aldehyde ranging from 0.01 to 0.0001, and preferably being about 0.001. The buffer is used in aqueous solution such that the cyanohydrin formed is, preferably, in a weight concentration of about 50% on leaving the column.

Figure 1:
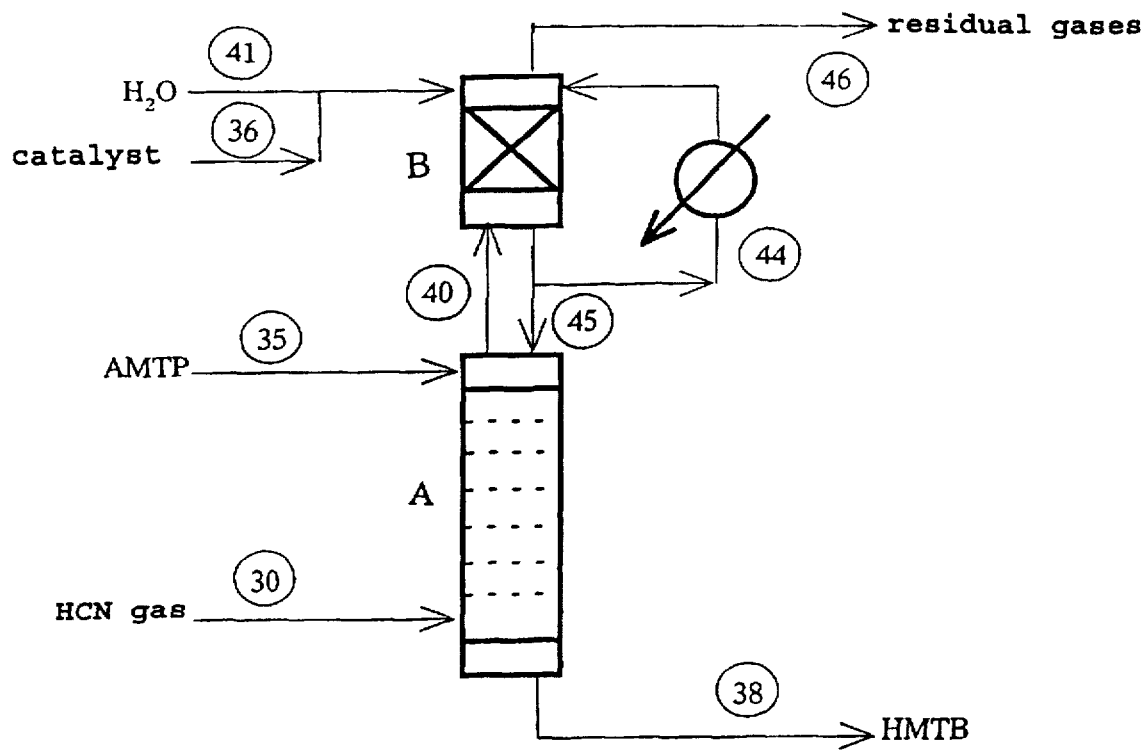
FIG. 1 is a schematic representation of one embodiment of the process according to the present invention.

The reaction may be carried out, as mentioned above, between a gas and a liquid, i.e., aqueous solution. In this case, the reaction is preferably carried out in a gas-liquid contact device such as: a column with plates, a column with packing, a bubble column, a tubular reactor, a drip column, a reactor with a mechanically stirred tank, or a reactor with a submerged jet.

According to the first implementation device, i.e., a reactive absorption column with plates, which is a preferred device in accordance with carrying out the present invention, the gas flow containing the hydrogen cyanide is introduced at the foot of the plate column and the buffered aqueous solution of aldehyde is introduced at the column head. In place of the aqueous solution of aldehyde, it is possible to introduce independent flow inlets at the column head, that is to say a water inlet, an aqueous buffered solution inlet, and an aldehyde solution inlet. It is obvious that a person skilled in the art will adapt the number of flows to the device which he intends to use.

In the above-discussed preferred embodiment, an additional washing column is installed at the head of the reactive absorption column in order to recover the remaining aldehyde and the traces of unreacted hydrogen cyanide from the gases leaving the reactive absorption column. This washing column allows exchange between the gases introduced at the foot and the water introduced at the head. For this washing, it is possible to use, for example, columns with plates or columns with packing. The water recovered at the foot of this column is advantageously re-introduced into the reactive absorption column and the purified gases are conveyed to an incinerator.

If the reaction is carried out between an aqueous solution of hydrogen cyanide and an aldehyde, the reaction is preferably performed in a tubular reactor such as an adiabatic piston reactor.

In all cases, the reaction is rapid and exothermic.

According to the above-discussed first preferred embodiment of the invention, i.e., a reaction between a gas and a liquid, i.e., aqueous solution, the reaction is preferably carried out at a temperature ranging from 50° to 100° C., and more preferably being about 70° C.; and at atmospheric pressure when performed in an open column. The temperature is regulated by the amount of water introduced with the buffer.

When the process is performed in a tubular reactor, according to the second preferred embodiment of the invention, the temperature preferably ranges from 30° to 110° C., and the pressure preferably ranges from 1 to 10 bar.

The cyanohydrin of the starting aldehyde, obtained by any one of the embodiments of the invention and especially the cyanohydrin of methylthiopropionic aldehyde, is either aminated or treated with a mixture of ammonia and carbon dioxide in order to lead subsequently to methionine, or is hydrolysed directly to methylthio-α-hydroxybutyric acid.

The present invention will be described more fully with the aid of the examples which follow, which should not be considered as limitations of the invention.

EXAMPLE 1

First Embodiment of the Invention

An Oldershaw column (A) being 50 mm in diameter, 1 meter in height and equipped with 20 perforated plates, and a packed column (B) of the same diameter, 20 cm in height and equipped with a multiknit packing were used. A schematic representation of this device is attached (see FIG. 1).

1556.2 g/h of a crude hydrogen cyanide synthesis gas were introduced into column A via the feed 30, this gas contained by weight:

Methylthiopropionic aldehyde was introduced into column A at a flow rate of 408.36 g/h via the feed 35; via the feed 41 at the head of column B were introduced 150 g/h of water; and via the feed 36 were introduced 4.89 g/h of a mixture of 1.13 g of citric acid and 0.49 g of sodium hydroxide.

1013 g/h of an aqueous solution (38) was collected at the foot of column A, this solution contained:

| 2-hydroxymethylthiobutyronitrile | 514.25 |
| HCN | 1.54 |
| methylthiopropionic aldehyde | 0.04 |
| $H_2O$ | 495.85 |
| citric acid | 1.13 |
| sodium hydroxide | 0.49 |

The gases leaving column A were conveyed to column B via 40 at a flow rate of 1531 g/h and exited column B via 46 at a flow rate of 1106 g/h, these gases consisted of:

| HCN | 1.65 |
| $CH_4$ | 0.77 |
| CO | 88.45 |
| $CO_2$ | 33.02 |
| $H_2$ | 18.12 |
| $N_2$ | 895.46 |
| $H_2O$ | 60.68 |
| various | 8.52 |

These gases were conveyed to the incinerator. A feedback flow (flow 44) of 11181.91 g/h of a cooled aqueous solution was set up in column B, towards the top of the column, this solution contained:

| HCN | 3.90 |
| $N_2$ | 7.72 |
| $H_2O$ | 10434.91 |
| methylthiopropionic aldehyde | 0.09 |
| hydroxymethylthiobutyronitrile | 703.59 |
| citric acid | 22.12 |
| sodium hydroxide | 9.59 |

An aqueous solution having the same composition as the feedback solution of column B was conveyed from the outlet of column B (flow 45) to the column A, at a flow rate of 580.06 g/h.

EXAMPLE 2

Adjustment of the NaOH/citric Acid Molar Ratio

Example 1 was repeated, having modified the value of the pH. The degree of conversion of the methylthiopropionic aldehyde was measured, on different plates of the column, as a function of the pH.

| | pH 5.6 | pH 4.7 | pH 3.6 | pH 4.5 | pH 5.2 |
|---|---|---|---|---|---|
| 2nd plate | 50.32 | 38.31 | 39.00 | 47.29 | 73.92 |
| 4th plate | 95.74 | 53.48 | 47.17 | 49.82 | 82.21 |
| 7th plate | 100.00 | 96.15 | 70.09 | 69.86 | 98.79 |
| 9th plate | 100.00 | 99.86 | 75.76 | 73.92 | 99.95 |
| 11th plate | 100.00 | 99.94 | 84.21 | 84.17 | 99.99 |
| 13th plate | 100.00 | 99.96 | 90.84 | 99.63 | 100.00 |
| 15th plate | 100.00 | 99.98 | 98.48 | 99.93 | 100.00 |
| 17th plate | 100.00 | 100.00 | 98.30 | 99.95 | 100.00 |
| 19th plate | 100.00 | 100.00 | 99.27 | 99.87 | 100.00 |

The hydroxymethylthiobutyronitrile solutions obtained after the reaction were introduced into an oven maintained at 70° C. in order to study the degradation of the nitrile as a function of time. The degradation was estimated by measuring the APHA coloration according to the ISO international standard 2211-1973.

| Buffer pH | pH 5.6 | pH 4.7 | pH 3.6 | pH 4.5 | pH 5.2 |
|---|---|---|---|---|---|
| pH of the nitrile | 7.2 | 5.2 | 3.8 | 4.7 | 6.6 |
| Degradation duration (h) | 4 | 48 | 48 | 48/72 | 72 |
| APHA coloration before degradation | 966 | 190 | 300 | 238 | 881 |
| APHA coloration after degradation | 17380 | 1071 | 1642 | 333/2837 | 8769 |

EXAMPLE 3

Synthesis of 2-hydroxymethylthiobutyronitrile

The following were loaded with stirring into a 150 ml jacketed glass reactor:

| methylthiopropionic aldehyde | 47.43 g |
|---|---|
| water | 30.97 g |

The medium was heterogeneous (2 immiscible liquid phases). 0.6669 g of catalytic solution was added. The catalytic solution was obtained by mixing:

| NaOH | 9 g |
|---|---|
| citric acid | 20.77 g |
| water | 70.30 g |

The temperature of the medium was established at about 20° C. The pH imposed by the catalytic system was in the region of 5.

42.37 g of an aqueous solution of hydrogen cyanide at a concentration of 30.70% by mass was introduced as quickly as possible via a dropping funnel. The temperature of the reaction medium rose instantaneously to 70° C. This corresponded to the heat of reaction. The temperature level (70° C.) was maintained in the reaction mass for a period of 5 minutes by circulating a hot fluid through the jacket.

The pH remained at about 5 throughout the reaction. After this time spent at 70° C., it was verified that the yield of the reaction for the synthesis of methylthiobutyronitrile relative to the methylthiopropionic aldehyde was 100%.

The reaction medium became homogeneous as soon as the temperature and the level of conversion of the methylthiopropionic aldehyde reached a sufficient level.

EXAMPLE 4

Second Embodiment of the Invention

Figure 2:
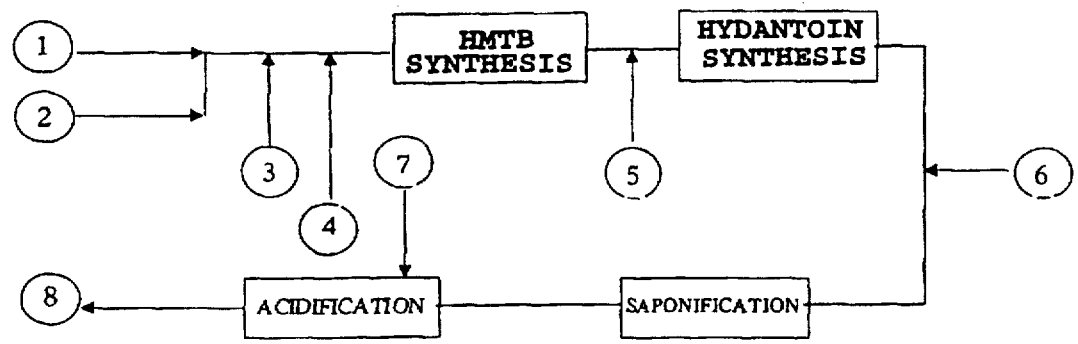
FIG. 2 is a schematic representation of one embodiment of the process according to the present invention.

Methylthiopropionic aldehyde was condensed continuously, in an adiabatic reactor, with an aqueous solution of hydrogen cyanide at a concentration of 20%. This solution was prepared from liquid 100% hydrogen cyanide and water. The reaction catalyst was added straight into the water. According to the schematic representation of FIG. 2, the water was introduced at a flow rate of 1941 kg/h 1 the citric acid/sodium citrate catalyst at a flow rate of 10kg/h 2, the 20% solution of hydrogen cyanide at a flow rate of 398 kg/h 3 and the methylthiopropionic aldehyde 4 at a flow rate of 1444 kg/h.

The catalytic solution 2 was prepared by adding 390 g of aqueous 50% sodium hydroxide and 450 g of anhydrous citric acid into 1340 g of water. The pH of the solution was adjusted to 5.0±0.2 by adding one or other of the two reactants.

The hydroxymethylthiobutyronitrile that was formed was then reacted with the ammoniacal waters 5 which were introduced at a flow rate of 8400 kg/h. These ammoniacal waters contained 13.7% by mass of carbon dioxide, 9.7% by mass of ammonia and water. The hydantoin that was formed was hydrolysed with an aqueous solution of sodium hydroxide at a concentration of 50% by weight, which was introduced at a flow rate of 2310 kg/h 6. The sodium methioninate was hydrolysed to methionine by the action of 98% sulphuric acid, which was introduced at 7 at a flow rate of 2890 kg/h. An aqueous solution containing 15% of methionine by weight was collected at 8 at a flow rate of 1986 kg/h. The yield of methionine relative to the methylthiopropionic aldehyde was 96.0%.

What is claimed is:

1. A condensation reaction process, which comprises condensing an aldehyde with hydrogen cyanide in the presence of a buffer wherein said buffer allows the condensation reaction to occur at a pH equal to or above 4.0 and without the presence of amines.

2. A process according to claim 1, wherein the pH of said reaction ranges from 4.0 to 6.0.

3. A process according to claim 2, wherein the pH of said reaction is about 5.

4. A process according to claim 1, wherein said buffer is non-volatile and non-toxic.

5. A process according to claim 1, wherein said buffer is a mixture of at least one acid and at least one alkaline salt of an acid or is a mixture of at least one acid and at least one alkaline hydroxide.

6. A process according to claim 5, wherein said buffer is selected from the following mixtures of buffers: citric acid and sodium citrate; citric acid and sodium hydroxide; phosphoric acid and sodium hydrogen phosphate; phosphoric acid and sodium hydroxide; succinic acid and sodium succinate; succinic acid and sodium hydroxide; acetic acid and sodium acetate; acetic acid and sodium hydroxide; and potassium hydrogen phthalate and sodium hydroxide.

7. A process according to claim 6, wherein said buffer is a mixture of citric acid and sodium citrate.

8. A process according to claim 7, wherein said buffer is prepared in situ by neutralization of citric acid with sodium hydroxide wherein said citric acid and said sodium hydroxide are present in a molar ratio ranging from 0.3 to 0.7.

9. A process according to claim 8, wherein said molar ratio of citric acid to sodium hydroxide is about 0.5.

10. A process according to claim 1, wherein said aldehyde is an aliphatic aldehyde containing from 1 to 6 carbon atoms that may be unsubstituted or substituted with an alkyl, alkoxy or alkylthio group.

11. A process according to claim 10, wherein said aldehyde is methylthiopropionic aldehyde.

12. A process according to claim 1, wherein said condensation reaction is a reactive absorption reaction between a liquid aldehyde and a gaseous hydrogen cyanide.

13. A process according to claim 12, wherein said reactive absorption reaction takes place in a gas-liquid contact device selected from: a column with plates, a column with packing, a bubble column, a tubular reactor, a drip column, a reactor with a mechanically stirred tank, and a reactor with a submerged jet.

14. A process according to claim 13, wherein said reactive absorption reaction is carried out using a column with plates which is a reactive absorption column.

15. A process according to claim 14, further comprising a washing column added to the head of said reactive absorption column.

16. A process according to claim 12, wherein said gaseous hydrogen cyanide contains about 7% by volume of hydrogen cyanide.

17. A process according to claim 1, wherein said condensation reaction is a reaction between a liquid aldehyde and an aqueous solution of hydrogen cyanide.

18. A process according to claim 17, wherein said reaction takes place in an adiabatic piston reactor.

19. A process according to claim 17, wherein said aqueous solution of hydrogen cyanide contains about 20% by weight of hydrogen cyanide.

20. A process according to claim 17, wherein the molar ratio between said aqueous solution of hydrogen cyanide and said liquid aldehyde is a molar excess ranging from 0.1 to 10%.

21. A process according to claim 20, wherein said molar ratio is a molar excess ranging from 2 to 5%.

* * * * *